(12) United States Patent
Mirejovsky et al.

(10) Patent No.: US 6,906,047 B2
(45) Date of Patent: Jun. 14, 2005

(54) AQUEOUS IFOSFAMIDE COMPOSITION

(75) Inventors: Dorla Mirejovsky, Irvine, CA (US); Michael Burkhart, Glendora, CA (US)

(73) Assignee: Gensia Sicor Pharmaceuticals, Inc., Irvine, CA (US)

(*) Notice: Subject to any disclaimer, the term of this patent is extended or adjusted under 35 U.S.C. 154(b) by 0 days.

(21) Appl. No.: 10/319,377

(22) Filed: Dec. 13, 2002

(65) Prior Publication Data

US 2003/0229052 A1 Dec. 11, 2003

Related U.S. Application Data

(60) Provisional application No. 60/340,325, filed on Dec. 13, 2001.

(51) Int. Cl.$^7$ ................................................. A61K 31/66
(52) U.S. Cl. ....................................... 514/109; 558/199
(58) Field of Search ......................................... 514/109

(56) References Cited

FOREIGN PATENT DOCUMENTS

| WO | 9507083 | * | 9/1995 |
|---|---|---|---|
| WO | 9918973 | * | 4/1999 |

OTHER PUBLICATIONS

HCAPLUS, DN 130:316628, Bayer, WO 9918973, (1999), abstract only.*

* cited by examiner

*Primary Examiner*—Christopher S. F. Low
*Assistant Examiner*—C. Delacroix-Muirheid
(74) *Attorney, Agent, or Firm*—Sutherland Asbill & Brennan LLP

(57) ABSTRACT

This invention is directed towards a ready-to-use aqueous composition of ifosfamide. In one embodiment, the invention is directed to an aqueous ifosfamide composition which comprises ifosfamide, a pharmaceutically acceptable buffer, and water. The concentration of ifosfamide in the composition may be between about 40 mM and about 400 mM. The concentration of buffer in the composition may be between about 10 mM and about 260 mM. The molar ratio of ifosfamide to buffer may be between about 0.5:1 to about 20:1. The pH of the composition may be between about 4 and about 8.

20 Claims, No Drawings

AQUEOUS IFOSFAMIDE COMPOSITION

RELATED APPLICATIONS

This application claims priority to and herein incorporates by reference in its entirety Mirejovsky, et al., U.S. Provisional Patent Application Ser. No. 60/340,325, filed Dec. 13, 2001, and entitled AQUEOUS IFOSFAMIDE COMPOSITION.

FIELD OF THE INVENTION

The invention relates to aqueous ifosfamide compositions, and to processes for their preparation.

BACKGROUND OF THE INVENTION

Ifosfamide is a chemotherapeutic agent chemically related to the nitrogen mustards and a synthetic analog of cyclophosphamide. Ifosfamide is the drug whose chemical name is 3-(2-chloroethyl)-2-[(2-chloroethyl amino)]-tetrahydro-2H-1,3,2-oxazaphosphorin-2-oxide. It belongs to a group of chemical compounds denoted oxazaphorines, which are presently in use as therapeutic agents for the treatment of tumors. Ifosfamide is presently used in combination with certain other antineoplastic agents, and is a third line chemotherapeutic for the treatment of testicular cancers derived from germ cells. Generally, it is used in conjunction with a hemorrhagic prophylactic agent, such as mesna.

The solubility of ifosfamide is about 10% by weight in water, the aqueous solutions only being of limited shelf-life at room temperature. Ifosfamide solutions are administered parenterally at a maximum concentration of the aqueous solution of 5% (50 mg/mL).

It is desirable to provide a ready-to-use stable aqueous ifosfamide composition that could be administered without the need for reconstituting ifosfamide sterile powder currently available or a lyophilized ifosfamide composition. However, an impediment to the preparation of an aqueous ifosfamide composition is that such compositions may not be adequately stable at ambient temperatures. Generally, ready-to-use solutions are stored and transported at refrigerated temperatures (e.g., 2° C.–8° C.) to circumvent the lower stability of ready-to-use solutions in comparison to powder or lyophilized compositions. Still, accidental exposure of a ready-to-use ifosfamide composition to elevated temperatures (i.e., temperatures at or above ambient temperature) during storage or transportation can result in unacceptable levels of degradation.

An object of the present invention is to provide a ready-to-use aqueous ifosfamide composition with enhanced stability at elevated temperatures such that accidental exposure of the composition to elevated temperatures for a brief time would be less likely to result in unacceptable levels of degradation of the ifosfamide.

SUMMARY OF THE INVENTION

The present inventors have found, surprisingly, that it may be possible to prepare aqueous compositions containing ifosfamide having enhanced stability upon a transient exposure to elevated temperatures by controlling the molar ratio of ifosfamide to buffer.

This invention is directed towards a ready-to-use aqueous composition of ifosfamide. In one embodiment, the invention is directed to an aqueous ifosfamide composition which comprises ifosfamide, a pharmaceutically acceptable buffer, and water. The concentration of ifosfamide in the composition may be between about 40 mM and about 400 mM. The concentration of buffer in the composition may be between about 10 mM and about 260 mM. The molar ratio of ifosfamide to buffer may be between about 0.5:1 and about 20:1. The pH of the composition may be between about 4 and about 8.

In another embodiment, the invention is directed to a method for preparing an aqueous ifosfamide composition according to the present invention. The method comprises combining ifosfamide, water, and a pharmaceutically acceptable buffer to provide a composition having between about 40 mM and about 400 mM ifosfamide, between about 10 mM and about 260 mM of a pharmaceutically acceptable buffer, water, and a pH between about 4 and about 8.

DETAILED DESCRIPTION OF THE INVENTION

The present invention is based on the discovery that an aqueous ifosfamide composition having enhanced stability at elevated temperatures may be prepared by controlling the molar ratio of ifosfamide to buffer in the composition. The present invention is directed to an aqueous ifosfamide composition comprising ifosfamide, a pharmaceutically acceptable buffer, and water.

As used herein, the term "elevated temperatures" refers to temperatures at or above ambient temperatures. The term "ambient temperature" refers to temperatures ranging from about 22° C. to about 28° C. The term "enhanced stability" refers to an aqueous ifosfamide composition which, when compared to another aqueous ifosfamide composition, retains at least 5% by weight more of the original amount of ifosfamide present when both compositions are subjected to the same temperature conditions over a given period of time. For example, the term "enhanced stability" may be used to distinguish between two otherwise comparable aqueous ifosfamide compositions as follows: Two aqueous ifosfamide compositions, A and B, differ only in the concentration of buffer present, and therefore in the molar ratio of ifosfamide to buffer. Compositions A and B have buffer concentrations of 32.5 mM and 0 mM, respectively. After storing both compositions at 27.5° C. for 3 months, composition A is found to contain 82% of the original amount of ifosfamide present, whereas composition B is found to contain 75% of the original amount of ifosfamide present. Composition A has "enhanced stability" with respect to composition B because composition B showed 25% degradation whereas composition A showed only 18% degradation. Thus, composition B showed 37% more degradation than composition A under the same conditions ((25%−18%)÷18%=39%).

The term "comparable aqueous ifosfamide composition" refers to an aqueous ifosfamide composition which differs from the reference aqueous ifosfamide composition only in the concentration of buffer, and consequently, in the molar ratio of ifosfamide to buffer. For example, in reference to an aqueous ifosfamide composition A, having an ifosfamide concentration of 200 mM and a buffer concentration of 32.5 mM, aqueous ifosfamide composition B, has an ifosfamide concentration of 200 mM and no buffer. Because composition B differs from composition A only in the concentration of buffer present, composition B would be a "comparable aqueous ifosfamide composition" with respect to composition A. If, on the other hand, composition B had an ifosfamide concentration other than 200 mM, then it would not be a "comparable aqueous ifosfamide composition" with respect to composition A.

In one embodiment, the concentration of ifosfamide in the composition may be between about 40 mM and about 400 mM. The concentration of buffer in the composition may be between about 10 mM and about 260 mM. The molar ratio of ifosfamide to buffer may be between about 0.5:1 to about 20:1. The pH of the composition may be between about 4.0 and about 8.0.

In one embodiment, the molar ratio of ifosfamide to buffer is between 1:1 and 10:1. Within this range, the molar ratio of ifosfamide to buffer may be between 2:1 and 8:1. Typically, the molar ratio of ifosfamide to buffer is between 3:1 and 6:1.

In another embodiment, the concentration of ifosfamide is between 100 mM and 300 mM. Within this range, the concentration of ifosfamide may be between 150 mM and 250 mM. Typically, the concentration of ifosfamide is between 185 mM and 215 mM (50 mg/mL is 191.5 mM).

In another embodiment, the concentration of buffer is between 10 mM and 100 mM. Within this range, the concentration of buffer may be between 20 mM and 80 mM. Typically the concentration of buffer is between 25 mM and 50 mM.

Pharmaceutically acceptable buffers which may be used in the compositions of the present invention include borate buffers, citrate buffers, phosphate buffers, citric acid/phosphate buffers, carbonate/carbonic acid buffers, succinate/succinic acid buffers, and tris(hydroxymethyl) aminomethane/hydrochloric acid buffers. Pharmaceutically acceptable carbonate buffers include $CaCO_3$, and $Na_2CO_3$. Pharmaceutically acceptable phosphate buffers include $Na_3PO_4$, $Na_2HPO_4$, $NaH_2PO_4$, $K_3PO_4$, $K_2HPO_4$, and $KH_2PO_4$. In one embodiment, the buffer is $Na_2HPO_4$/$NaH_2PO_4$. In another embodiment, the buffer is $K_2HPO_4$/$KH_2PO_4$.

The compositions of the present invention typically have a pH between about 4 and about 8. In one embodiment, the composition has a pH between 6.5 and 8.0. In another embodiment, the composition has a pH between 5 and 7.

In another embodiment, the invention is directed to a method for preparing an aqueous ifosfamide composition by (a) combining ifosfamide with water; and (b) combining the mixture of step (a) with a pharmaceutically acceptable buffer. Alternatively, the invention is directed to a method for preparing an aqueous ifosfamide composition by combining ifosfamide with a pharmaceutically acceptable buffered aqueous solution.

The aqueous ifosfamide compositions of the present invention may be useful for treating a diverse array of neoplastic diseases including small cell lung cancer, ovarian cancer, endometrial cancer, breast cancer, testicular cancer, Hodgkin's disease and soft tissue carcinoma. Ifosfamide may be useful in the treatment of human and other mammalian patients. It is also typically given with mesna to prevent urotoxicity.

The pharmaceutical compositions of the present invention are generally administered in the form of a daily dosage unit at concentrations from about 1 mg/kg of body weight to about 500 mg/kg of body weight. Typically the compositions of the present invention are administered in a daily dosage of from about 10 mg/kg to about 250 mg/kg. Most often the compositions of the present invention are administered in a daily dosage of from about 20 mg/kg to about 100 mg/kg. Chemotherapeutic agents often are administered in dosages based upon the surface area of the patient. Ifosfamide typically is administered at a dose of 1.2 $g/m^2$-per day for 5 consecutive days. As recognized by those skilled in the art, the particular quantity of pharmaceutical composition according to the present invention administered to a patient will depend upon a number of factors, including, without limitation, the biological activity desired, the condition of the patient, and tolerance for the drug. Typically, ifosfamide is administered intravenously over an infusion period of at least 30 minutes or by continuous IV infusion.

The present inventors have found, surprisingly, that it may be possible to prepare aqueous compositions containing ifosfamide having enhanced stability upon a transient exposure to elevated temperatures by controlling the molar ratio of ifosfamide to buffer. In order to prepare such compositions with enhanced stability at elevated temperatures, the molar ratio of ifosfamide to buffer may be from about 1:1 to about 10:1.

The effect of the molar ratio of ifosfamide to buffer on the stability of aqueous ifosfamide compositions at elevated temperatures is shown in the following tables. The concentration of ifosfamide in each of the compositions of Tables 1–4 was 191.5 mM (50 mg/mL). Table 5 specifies the concentration of ifosfamide in each of the compositions listed.

TABLE 1

Effect of Molar Ratio of Ifosfamide to Buffer on Recovery of Ifosfamide from Aqueous Ifosfamide Compositions Stored at Various Temperatures.

| Concentration of Buffer pH 7.4 | Ifosfamide to Buffer Molar Ratio | 3 Months | | 1 Month at 40° C. Followed by 2 Months at 2–8° C. | 6 Months | |
|---|---|---|---|---|---|---|
| | | 2–8° C. | 27.5° C. | | 2–8° C. | 27.5° C. |
| 32.5 mM | 5.9:1 | 100.9 | 80.5 | 62.7 | 101.1 | 62.3 |
| 65 mM | 2.9:1 | 101.0 | 80.7 | 64.1 | 100.7 | 64.7 |
| 130 mM | 1.5:1 | 101.2 | 80.7 | 63.9 | 102.4 | 66.3 |
| 195 mM | 1:1 | 102.1 | 79.9 | 63.2 | 102.1 | 62.8 |
| 260 mM | 0.7:1 | 100.6 | 78.6 | 60.7 | 95.1 | 63.9 |
| WFI | | 100.2 | 75.7 | 57.8 | 100.9 | 55.7 |

TABLE 2

Effect of Molar Ratio of Ifosfamide to Buffer on Recovery of Ifosfamide from Aqueous Ifosfamide Compositions Stored at Various Temperatures.

| Concentration of Buffer pH 7.4 | Ifosfamide to Buffer Molar Ratio | 3 Months 2–8° C. | 22° C. | 27.5° C. |
|---|---|---|---|---|
| 32.5 mM | 5.9:1 | 101.4 | 95.0 | 82.0 |
| 20 mM | 9.6:1 | 100.8 | 94.3 | 80.7 |
| 10 mM | 19.2:1 | 101.0 | 94.8 | 79.6 |
| WFI | | 100.1 | 92.0 | 75.4 |

TABLE 3

Effect of Exposure of Aqueous Ifosfamide Compositions to Ambient Temperature on Recovery of Ifosfamide.

| Concentration of Buffer pH 7.4 | % Recovery 3 Months at 22° C. followed by 34 Months at 2–8° C. | 37 Months at 2–8° C. |
|---|---|---|
| 32.5 mM | 97.4 | Not tested |
| 10 mM | 81.8 | 94.4 |
| WFI | 85.2 | 96.5 |

TABLE 4

Stability of Ifosfamide Composition in Glass and Polypropylene Vials.

| Composition | % Recovery after 36 Months at 2–8° C. Glass Vials | Polypropylene Vials |
|---|---|---|
| 32.5 mM pH 7.5 | 99.4 | 99.7 |
| 32.5 mM pH 6.5 | 99.2 | 99.3 |
| WFI | Not tested | 96.9 |
| 0.9% Saline | Not tested | 97.9 |

TABLE 5

Ifosfamide Recovery from Various Formulations of Aqueous Ifosfamide Injection Stored at Two Different Temperatures

| Composition | Ifosfamide Recovery, % 3 Months 2–8° C. | 22° C. | 8 Months 2–8° C. | 3 Months at 22° C. followed by 5 Months at 2–8° C. |
|---|---|---|---|---|
| Phosphate Buffer 50 mg/mL Ifosfamide, pH 6.5 (Actual pH) | | | | |
| 32.5 mM (6.5) | 100.6 | 85.3 | 99.0 | 90.6 |
| 130 mM (6.3) | 100.7 | 71.0 | 99.8 | 91.0 |
| 195 mM (6.2) | 101.2 | 83.3 | 99.2 | 90.8 |
| 260 mM (6.2) | 96.1 | 91.6 | 99.0 | 90.2 |
| Phosphate Buffer 10 mg/mL Ifosfamide, pH 6.5 (Actual pH) | | | | |
| 10 mM (7.4) | 100.6 | 90.0 | 100.0 | 93.0 |
| 32.5 mM (6.4) | 75.9 | 90.9 | 98.0 | 93.0 |
| 130 mM (6.2) | 75.4 | 90.1 | 99.0 | 90.0 |
| Phosphate Buffer 20 mg/mL Ifosfamide, pH 6.5 (Actual pH) | | | | |
| 10 mM (6.6) | 97.4 | 75.1 | 98.5 | 90.5 |
| 32.5 mM (6.4) | 98.3 | 91.6 | 100.0 | 92.5 |
| 130 mM (6.2) | 99.5 | 89.2 | 99.5 | 93.0 |
| TRIS pH 7.4 50 mg/mL Ifosfamide (Actual pH) | | | | |
| 10 mM (7.4) | 100.0 | 89.9 | 99.2 | 89.8 |
| 32.5 mM (7.5) | 89.3 | 93.4 | 100.8 | 92.8 |
| 195 mM (7.5) | 99.1 | 88.3 | 100.2 | 96.6 |
| Citrate pH 6.0 50 mg/mL Ifosfamide (Actual pH) | | | | |
| 10 mM (6.1) | 101.7 | 93.0 | 99.6 | 91.2 |
| 32.5 mM (6.3) | 99.6 | 92.5 | 98.2 | 90.6 |
| 195 mM (6.0) | 99.6 | 88.7 | 97.6 | 88.2 |

The data in Tables 1 and 2 demonstrate that the molar ratio of ifosfamide to buffer in aqueous ifosfamide compositions affects the stability of the compositions at elevated temperatures. The data in Tables 1 and 2 shows an enhancement of ifosfamide stability in buffered ifosfamide formulations as compared to the unbuffered ifosfamide formulation. For example, after 3 months at 27.5° C., the ifosfamide composition having 32.5 mM of buffer (i.e., a molar ratio of 6:1) contained 80.5% of the original amount of ifosfamide present. In contrast, after being stored for 3 months at 27.5° C., the ifosfamide composition in Water for Injection alone (i.e., no buffer) contained 75.7% of the original amount of ifosfamide present.

The data in Table 3 shows that a molar ratio above about 10:1 adversely affects the stability of the aqueous ifosfamide composition when exposed to an ambient temperature for transient period of time. For example, after exposing a composition having 191.5 mM of ifosfamide and 32.5 mM of buffer (i.e., a molar ratio of 6:1) for 3 months to 22° C., followed by storage at 2–8° C. for 34 months, the composition contained 97.4% of the original amount of ifosfamide present. In contrast, after exposing a composition having 191.5 mM of ifosfamide and 10 mM of buffer (i.e., a molar ratio of 19:1) for 3 months to 22° C., followed by storage at 2–8° C. for 34 months, the composition contained 81.8% of the original amount of ifosfamide present.

The data in Table 4 demonstrates that the ifosfamide compositions of the present invention are stable in glass as well as plastic vials.

Some of the data in Table 5 appear to be anomalous and may have resulted from experimental error. Nevertheless, as a whole the data in Table 5 show favorable ifosfamide stability in buffered ifosfamide formulations at elevated temperatures.

The aqueous ifosfamide compositions of the present invention may be stored in any suitable container that does not adversely affect the stability of the compositions. For example, suitable containers for the compositions of the present invention include glass vials and plastic vials. Suitable plastic vials include those made primarily of polypropylene, Daikyo Resin CZ (sold by Daikyo Gomu Seiko, Ltd., reported in some references as polymethylpentene) and polyethylene terephthalate.

EXAMPLE 1

An ifosfamide solution (50 mg/mL) with pH of 7.3 was prepared by the following steps: Sodium phosphate monobasic, monohydrate (1.035 mg) and sodium phosphate dibasic, anhydrous (3.55 mg) were added to Water for Injection with stirring. Solid ifosfamide (50 mg) was added with stirring to the buffer solution. Water for Injection was added to bring the volume total to 1 mL.

EXAMPLE 2

An ifosfamide solution (50 mg/mL) with pH of 6.5 was prepared by the following steps: Sodium phosphate monobasic, monohydrate (3.45 mg) and sodium phosphate dibasic, anhydrous (1.065 mg) were added to Water for Injection with stirring. Solid ifosfamide (50 mg) was added with stirring to the buffer solution. Water for Injection was added to bring the volume total to 1 mL.

FORMULATION EXAMPLE 1

An aqueous solution containing an ifosfamide concentration of 50 mg/mL and having the following components:

| | |
|---|---|
| Ifosfamide | 50 mg/mL |
| Sodium phosphate monobasic, monohydrate | 1.035 mg/mL |
| Sodium phosphate dibasic, anhydrous | 3.55 mg/mL |
| Water for Injection | q.s. to 1 mL |

While 50 mg/mL ifosfamide composition has been exemplified, solutions of different concentrations of ifosfamide may be prepared according to the methods of the present invention.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following non-limiting enumerated embodiments.

What is claimed is:

1. An aqueous pharmaceutical composition consisting essentially of:
   (a) between 40 mM and 400 mM ifosfamide;
   (b) between 10 mM and 260 mM of a buffer; and
   (c) water;
   wherein the molar ratio of ifosfamide to buffer is in the range of about 0.5:1 to about 20:1.

2. A pharmaceutical composition according to claim 1, wherein said ratio of ifosfamide to buffer is in the range of 1:1 to 10:1.

3. A pharmaceutical composition according to claim 2, wherein said composition has enhanced stability at a temperature between 20° C. and 30° C. as compared to a comparable aqueous ifosfamide composition having an ifosfamide to buffer ratio less than 0.5:1 or greater than 20:1.

4. A pharmaceutical composition according to claim 2, wherein said composition has a pH between about 4.0 and about 8.0.

5. A pharmaceutical composition according to claim 2, wherein the concentration of ifosfamide is between 180 mM and 200 mM.

6. A pharmaceutical composition according to claim 5, wherein the concentration of said buffer is between 10mM and 100 mM.

7. A pharmaceutical composition according to claim 6, wherein the concentration of said buffer is between 20 mM and 80 mM.

8. A pharmaceutical composition according to claim 6, wherein said buffer is selected from the group of carbonate buffers, borate buffers, citrate buffers, phosphate buffers, citric acid/phosphate buffers, carbonate/carbonic acid buffers, succinate/succinic acid buffers, tris(hydroxymethyl)aminomethane/hydrochloric acid buffers and mixtures thereof.

9. A pharmaceutical composition according to claim 8, wherein said buffer is a phosphate buffer.

10. An aqueous pharmaceutical composition consisting essentially of:
    (a) between 170mM and 210 mM ifosfamide;
    (b) between 10 mM and 260 mM a phosphate buffer; and
    (c) water;
    wherein the molar ratio of ifosfamide to buffer is in the range of about 0.5:1 to about 20:1.

11. A pharmaceutical composition according to claim 10, wherein said ratio of ifosfamide to buffer is in the range of 1:1 to 10:1.

12. A pharmaceutical composition according to claim 11, wherein said composition has enhanced stability at a temperature between 20° C. and 30° C. as compared to a comparable aqueous ifosfamide composition having an ifosfamide to buffer ratio less than 0.5:1 or greater than 20:1.

13. A pharmaceutical composition according to claim 11, wherein said composition has a pH between about 4.0 and about 8.0.

14. A pharmaceutical composition according to claim 13, wherein said composition has a pH between about 5.5 and about 7.5.

15. A pharmaceutical composition according to claim 11, wherein the concentration of ifosfamide is between 180 mM and 200 mM.

16. A pharmaceutical composition according to claim 15, wherein the concentration of said buffer is between 10 mM and 100 mM.

17. A pharmaceutical composition according to claim 15, wherein the concentration of said buffer is between 20 mM and 80 mM.

18. A pharmaceutical composition according to claim 15, wherein said buffer is selected from the group of $Na_2HPO_4$, $NaH_2PO_4$, $K_2HPO_4$, $KH_2PO_4$ and mixtures thereof.

19. A pharmaceutical composition according to claim 18, wherein said buffer comprises $Na_2HPO_4$ and $NaH_2PO_4$.

20. A pharmaceutical composition according to claim 18, wherein said buffer comprises $K_2HPO_4$ and $KH_2PO_4$.

* * * * *